US00PP22327P2

(12) United States Plant Patent
Pineau

(10) Patent No.: US PP22,327 P2
(45) Date of Patent: Dec. 13, 2011

(54) ***PRUNUS* PLANT NAMED 'GREENTORCH'**

(50) Latin Name: *Prunus laurocerasus*
Varietal Denomination: Greentorch

(75) Inventor: Patrick Pineau, Beaufort en Vallée (FR)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/925,596

(22) Filed: Oct. 25, 2010

(51) Int. Cl.
*A01H 5/00* (2006.01)

(52) U.S. Cl. ..... Plt./226

(58) Field of Classification Search ..... Plt./226
See application file for complete search history.

*Primary Examiner* — Kent L Bell
(74) *Attorney, Agent, or Firm* — C. A. Whealy

(57) ABSTRACT

A new and distinct cultivar of *Prunus* plant named 'Greentorch', characterized by its erect plant habit; columnar plant form; dense and bushy habit; moderately vigorous to vigorous growth habit; and glossy dark green-colored leaves.

2 Drawing Sheets

Botanical designation: *Prunus laurocerasus.*
Cultivar denomination: 'GREENTORCH'.

BACKGROUND OF THE INVENTION

The present invention relates to a new and distinct cultivar of *Prunus* plant, botanically known as *Prunus laurocerasus*, commercially referred to as Cherry Laurel and hereinafter referred to by the name 'Greentorch'.

The new *Prunus* plant is a product of a planned breeding program conducted by the Inventor in Beaufort en Vallée, France. The objective of the breeding program was to create new *Prunus* plants with erect plant habit.

The new *Prunus* plant originated from a self-pollination made by the Inventor in 2000 in Beaufort en Vallée, France of *Prunus laurocerasus* 'Otto Luyken', not patented. The new *Prunus* plant was discovered and selected by the Inventor as a single flowering plant within the progeny of the stated self-pollination in a controlled environment in Beaufort en Vallée, France in 2002.

Asexual reproduction of the new *Prunus* by softwood cuttings in a controlled environment in Beaufort en Vallée, France since Sep. 1, 2002, has shown that the unique features of this new *Prunus* plant are stable and reproduced true to type in successive generations.

SUMMARY OF THE INVENTION

Plants of the new *Prunus* plant have not been observed under all possible environmental conditions. The phenotype may vary somewhat with variations in environment such as temperature and light intensity without, however, any variance in genotype.

The following traits have been repeatedly observed and are determined to be the unique characteristics of 'Greentorch'. These characteristics in combination distinguish 'Greentorch' as a new and distinct cultivar of *Prunus* plant:

1. Erect plant habit and columnar plant form.
2. Moderate branching habit; dense and bushy habit.
3. Moderately vigorous to vigorous growth habit.
4. Glossy dark green-colored leaves.

Plants of the new *Prunus* can be compared to the parent, 'Otto Luyken'. Plants of the new *Prunus* differ primarily from plants of 'Otto Luyken' in the following characteristics:

1. Plants of the new *Prunus* are more compact and more erect than plants of 'Otto Luyken'.
2. Plants of the new *Prunus* were more vigorous than plants of 'Otto Luyken'.
3. Leaves of plants of the new *Prunus* are shorter, broader, lighter green in color and glossier than leaves of plants of 'Otto Luyken'.

Plants of the new *Prunus* can also be compared to *Prunus laurocerasus* 'Herbergii', not patented. In side-by-side comparisons, plants of the new *Prunus* differ primarily from plants of 'Herbergii' in the following characteristics:

1. Plants of the new *Prunus* are more columnar than plants of 'Herbergii'.
2. Leaves of plants of the new *Prunus* are shorter and broader than leaves of plants of 'Herbergii'.

BRIEF DESCRIPTION OF THE PHOTOGRAPHS

The accompanying colored photographs illustrate the overall appearance of the new *Prunus* plant showing the colors as true as it is reasonably possible to obtain in colored reproductions of this type. Colors in the photographs may differ slightly from the color values cited in the detailed botanical description which accurately describe the colors of the new *Prunus* plant.

The photograph on the first sheet comprises a side perspective view of a typical plant of 'Greentorch' grown in a container.

The photograph on the second sheet is a close-up view of a typical stem and leaves of 'Greentorch'.

DETAILED BOTANICAL DESCRIPTION

The aforementioned photographs and following observations, measurements and values describe plants grown during the winter in 26-cm containers in an outdoor nursery in Beaufort en Vallée, France. Plants were grown under typical *Prunus* commercial practices with day temperatures ranging from 6° C. to 20° C. and night temperatures ranging from 1° C. to 15° C. Plants were three years old when the photographs and description were taken. In the following description, color references are made to The Royal Horticultural Society Colour Chart, 2007 Edition, except where general terms of ordinary dictionary significance are used.

Botanical classification: *Prunus laurocerasus* 'Greentorch'.

Parentage: Self-pollination of *Prunus laurocerasus* 'Otto Luyken', not patented.

Propagation:

*Type.*—By softwood cuttings.

*Time to initiate roots, winter.*—About two months at 15° C.

*Time to develop a rooted plant, winter.*—About six months at 10° C.

*Root description.*—Fibrous, thick; white in color.

*Rooting habit.*—Moderate branching; medium density.

Plant description:

*Plant form/habit.*—Evergreen perennial shrub; erect plant habit and columnar plant form; moderate branching habit; dense and bushy habit; moderately vigorous to vigorous growth habit.

*Plant height.*—About 132.2 cm.

*Plant width* (*spread*).—About 55.6 cm.

*Lateral branches.*—Quantity per plant: About 21. Length: About 47.8 cm. Diameter: About 5 mm. Internode length: About 2.3 cm. Strength: Strong. Texture: Smooth, glabrous. Color, developing: Close to 144C. Color, developed: Close to 199B to 199C.

Foliage description:

*Arrangement.*—Alternate, simple.

*Length.*—About 10.4 cm.

*Width.*—About 4.2 cm.

*Shape.*—Obovate to elliptic.

*Apex.*—Abruptly acute to short apiculate.

*Base.*—Attenuate.

*Margin.*—Shallow serrations; revolute.

*Texture, upper and lower surfaces.*—Smooth, glabrous.

*Luster.*—Glossy.

*Glands.*—Location: On lower leaf surfaces near the leaf base. Quantity: Two to four per leaf Shape: Circular. Diameter: About 1 mm. Color: Close to 146A.

*Venation pattern.*—Pinnate.

*Color.*—When developing, upper surface: Slightly darker than 143A. When developing, lower surface: Close to 144B. Fully developed, upper surface: Darker than between N137A and 147A; venation, close to 144B to 144C. Fully developed, lower surface: Close to 146C to 146D; venation, close to 144B.

*Petiole.*—Length: About 1.2 cm. Diameter: About 3 mm. Texture, upper and lower surfaces: Smooth, glabrous. Color, upper and lower surfaces: Close to 144C and 145A.

Flower description: Flower initiation and development has not been observed on plants of the new *Prunus*.

Disease/pest resistance: Plants of the new *Prunus* have not been noted to be resistant to pathogens and pests common to *Prunus*.

Garden performance: Plants of the new *Prunus* have been observed to have good garden performance and tolerate rain and wind. Plants of the new *Prunus* have been observed to be hardy to USDA Hardiness Zone 6 and to tolerate high temperatures of about 35° C.

It is claimed:

1. A new and distinct *Prunus* plant named 'Greentorch' as illustrated and described.

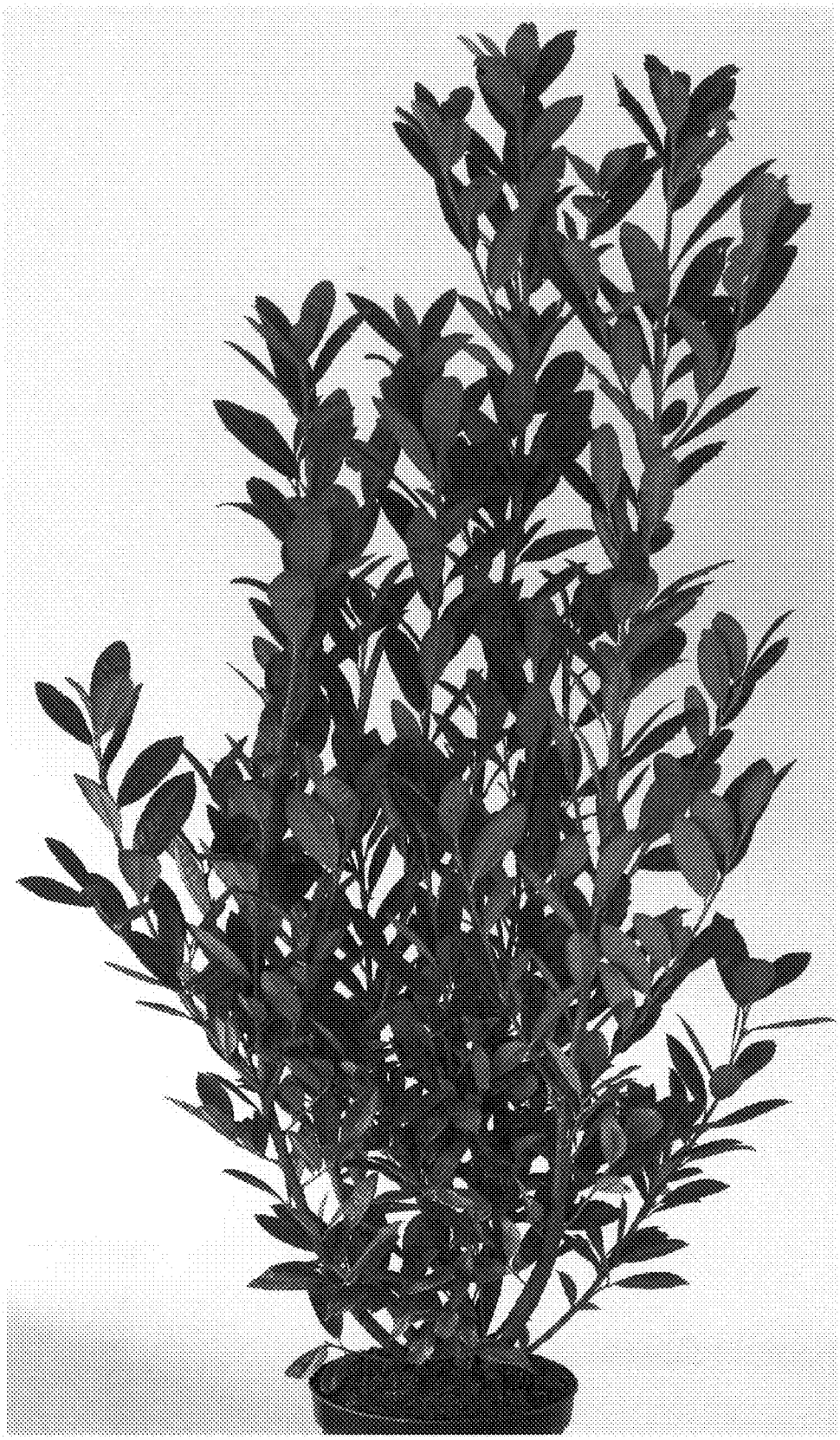

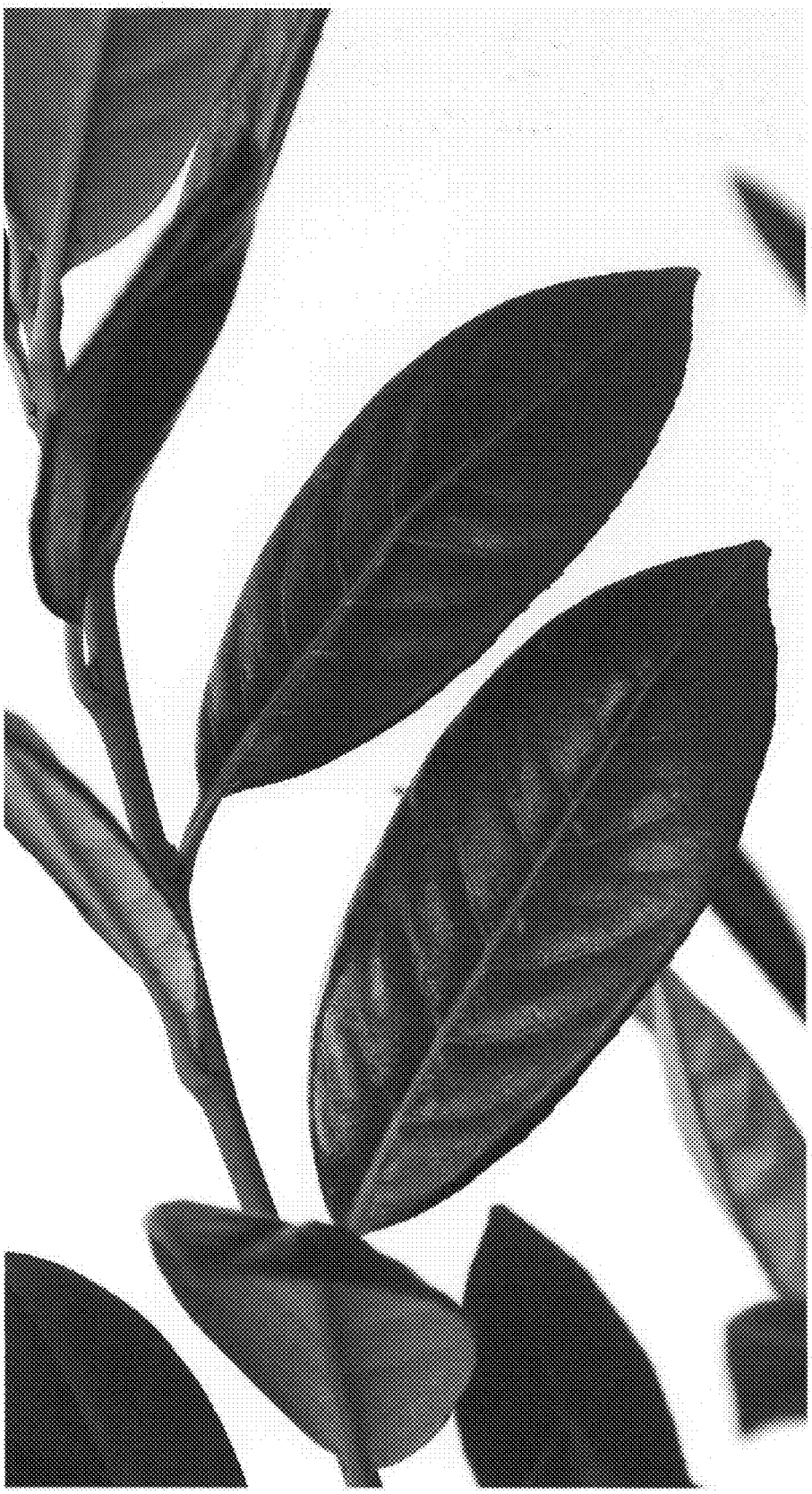

* * * * *